(12) United States Patent
Sowards et al.

(10) Patent No.: US 12,106,840 B2
(45) Date of Patent: Oct. 1, 2024

(54) SYSTEM AND METHOD FOR CONTROLLING OPERABILITY OF MULTIPLE MEDICAL DEVICES

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 668 days.

(21) Appl. No.: 17/205,979

(22) Filed: Mar. 18, 2021

(65) Prior Publication Data

US 2021/0295978 A1 Sep. 23, 2021

Related U.S. Application Data

(60) Provisional application No. 62/991,782, filed on Mar. 19, 2020.

(51) Int. Cl.
*G16H 20/40* (2018.01)
*A61B 8/08* (2006.01)
(Continued)

(52) U.S. Cl.
CPC ........... *G16H 20/40* (2018.01); *A61B 8/0833* (2013.01); *A61M 25/0152* (2013.01); *G16H 40/60* (2018.01); *A61B 5/062* (2013.01); *A61B 5/065* (2013.01); *A61B 2560/045* (2013.01); *A61B 2562/225* (2013.01); *A61M 2205/3306* (2013.01); *A61M 2205/502* (2013.01); *A61M 2205/583* (2013.01)

(58) Field of Classification Search
CPC ....... A61B 8/0833; A61B 5/062; A61B 5/065; A61B 2560/045; A61B 2562/225
See application file for complete search history.

(56) References Cited

U.S. PATENT DOCUMENTS 10,159,531 B2 12/2018 Misener et al.
2012/0165661 A1* 6/2012 Kemp .................. A61B 5/0059
600/427

(Continued)

FOREIGN PATENT DOCUMENTS

WO 2012138874 A2 10/2012
WO 2021/188826 A1 9/2021

OTHER PUBLICATIONS

PCT/US2021/023020 filed Mar. 18, 2021 International Search Report and Written Opinion dated Sep. 23, 2021.

*Primary Examiner* — Dixomara Vargas
(74) *Attorney, Agent, or Firm* — Rutan & Tucker LLP (57) ABSTRACT

An apparatus device features a housing; an input/output (I/O) interface, and one or more control logic units deployed to operate within the housing and communicatively coupled to the I/O interface. Each of the one or more control logic units can be configured to (i) control operations of at least one medical device controlled by a control logic unit of the one or more control logic units when the medical device is communicatively coupled to the I/O interface, and (ii) collect a subset of data acquired at least during placement of a vascular access device within a vasculature of a patient.

25 Claims, 8 Drawing Sheets

(51) Int. Cl.
    *A61M 25/01*     (2006.01)
    *G16H 40/60*     (2018.01)
    *A61B 5/06*     (2006.01)

(56) References Cited

U.S. PATENT DOCUMENTS

2014/0180087 A1    6/2014  Millett et al.
2018/0289927 A1* 10/2018  Messerly ................ G01L 1/242
2020/0000525 A1*  1/2020  Stigall .................... A61B 8/445

\* cited by examiner

SYSTEM AND METHOD FOR CONTROLLING OPERABILITY OF MULTIPLE MEDICAL DEVICES

PRIORITY

This application claims the benefit of priority to U.S. Provisional Application No. 62/991,782, filed Mar. 19, 2020, which is incorporated by reference in its entirety into this application.

BACKGROUND

Over the years, different types of technologies have been developed for guidance of vascular access devices such as catheters for example. The selection of the right type of intravascular guidance technology is based, at least in part, on an assessment of the patient's needs, vein anatomy, health, and medical history of the patient as well as consideration of the proposed treatment of a suspected diagnostic condition. In emergency situations, as time is of the essence, it is crucial for a health care facility (e.g., hospital, emergency clinic, etc.) to provide clinicians with access to a wide range of intravascular guidance technologies. Given that most of these intravascular guidance technologies are deployed as separate systems, health care facilities have been forced to purchase different types of intravascular guidance devices to provide an acceptable standard of care. The purchase of these systems imposes a large capital cost on the health care facility. Furthermore, these systems occupy floor space of the facility, where floor space is at a premium.

Disclosed herein is a data collection module that operates in combination with a central computing platform and provides connectivity to different types of medical devices, especially medical devices directed to different types of intravascular guidance technologies.

SUMMARY

Briefly summarized, one embodiment of the disclosure is directed to a customizable medical device monitoring system. Herein, the medical device monitoring system features a data collection module, which includes a first input/output (I/O) interface and a second I/O interface. The data collection module operates as an intermediary between a central computing platform communicatively coupled to the first I/O interface and one or more medical devices responsible for intravascular guidance (hereinafter, "medical device(s)") communicatively coupled to the second I/O interface. For example, the second I/O interface may be adapted to receive (i) a connector positioned at a proximal end of each medical device (e.g., connector located the proximal end of the medical device, the proximal end of an interconnect associated with the medical device, etc.) or (ii) a connector that operates as an intermediary between the second I/O interface and a connector associated with a selected medical device. For example, the intermediary connector may be a connector integrated within a sterile drape (e.g., a thru barrier/window (fiber optic) connector), which may provide a communicative coupling (e.g., mechanical, optical and/or electrical connection) to a medical device positioned on the sterile side of the drape. Alternatively, the data collection module may be configured to reside in the sterile environment (e.g., on sterile side of drape) with a thru barrier/window (fiber optic) connection that may be assisted by thru barrier palpation, lighting, and/or magnetic indicators/assists.

In some embodiments, the medical device(s) may accompany a vascular access device inserted into a vasculature (e.g., one or more blood vessels) of a patient or may be positioned outside of the patient. When accompanying a vascular access device within the vasculature of a patient, such as accompanying a catheter for example, the medical device is configured to collect a subset of data acquired during and after placement of the vascular access device. As an illustrative example, the collected data may include, but is not limited or restricted to: (i) vascularization data associated with the structure and/or content of a vasculature of a patient, (ii) intravascular guidance data associated with a physical state (e.g., length, shape, form, and/or orientation) of the medical device for guidance in the placement of the vascular access device, and/or (iii) data associated with a monitored system or organ within the patient. Of course, when the medical device is positioned outside of the patient, the collected data may focus on the intravascular guidance of the vascular access device, not the medical device per se, while vascularization and monitoring data may be collected as well.

The central computing platform is coupled to the first I/O interface of the data collection module via a wired or wireless interconnect. The central computing platform may be configured to conduct analytics on the collected data received from the data collection module, where the analytic results may be transmitted to a remotely located device for viewing or may be rendered on a display screen, integrated as part of or separate from the central computing platform, for review by a clinician. The selection as to which medical device is operational may be controlled through I/O selection logic. Examples of device selection may include, but are not limited or restricted to the following: (i) automatic device selection based on connectivity to the data collection module (e.g., the medical device(s) in operation are based on which devices are connected to the second I/O interface); (ii) manual device selection based on a user interface situated on the housing of the data collection module (or computing platform) and accessible to the clinician for manual selection as to which medical device is or which medical devices operational, or the like.

Another embodiment of the disclosure is directed to a central computing platform adapted with one or more connectors to establish operational communications with distinct data collection modules, where each data collection module pertains to a different intravascular guidance technology. For this embodiment, the central computing platform includes components that enable analytics of data provided by any of the data collection modules and each of these data collection modules is customized to include components that support communications requisite for a specific type of intravascular guidance technology offered by the medical device (or multiple medical devices) connected to that data collection module. The data collection modules are configured to collect data for use to determining placement and/or physical state of a vascular access device and may be used as a point of reference for plane identification/orientation (for spatial analysis) or central line identification and malposition identification associated with fiber optic shape sensing through placement of intrinsic sensors inscribed into one or more core fibers (which receive reflected light signals from which phase changes may determine malposition).

Furthermore, each of these data collection modules is removably coupled to the central computing platform, and thus, any data collection module may be removed, added to enhance functionality of the medical device monitoring system or substituted for another data collection module. This system architecture enables the central computing platform to support multiple types of medical devices that can be interchanged based on patient needs. The interchangeability offers a significant advantage from a cost perspective as different clinicians may use the same central computing platform and expand its functionality through the purchase of additional data collection modules. The interchangeability also provides a significant advantage to patient health as clinicians, in emergency situations, can immediately deploy different vascular access devices as patient health conditions change.

As an illustrative example, a first data collection module may include a first connector for use in establishing communications with and potentially receive power from the central computing platform. The first data collection module may further include a second connector that supports connectivity to a subset of the medical devices supported by the central computing platform, such as a single vascular access device supporting a specific intravascular guidance technology (e.g., fiber optics, electrical, ultrasound, spatial and/or magnetic) or multiple vascular access devices with complementary operability (e.g., fiber optics and electrical to provide for optical three-dimensional shape sensing, etc.). Alternatively, in lieu of the second connector, a medical device may be hardwired to the first data collection module.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Reference will now be made to figures wherein like structures will be provided with like reference designations. It is understood that the drawings are diagrammatic and schematic representations of exemplary embodiments of the invention, and are neither limiting nor necessarily drawn to scale.

Regarding terms used herein, it should be understood the terms are for the purpose of describing some particular embodiments, and the terms do not limit the scope of the concepts provided herein. Ordinal numbers (e.g., first, second, third, etc.) are generally used to distinguish or identify different components or operations, and do not supply a serial or numerical limitation. For example, "first," "second," and "third" components or operations need not necessarily appear in that order, and the particular embodiments including such components or operations need not necessarily be limited to the three components or operations. Similarly, labels such as "left," "side," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The terms "logic," "logic unit," and "component" are representative of hardware and/or software that is configured to perform one or more functions. As hardware, logic (or logic unit or component) may include circuitry having data processing and/or storage functionality. Examples of such circuitry may include, but are not limited or restricted to a processor, a programmable gate array, a microcontroller, an application specific integrated circuit, combinatorial circuitry, or the like. Alternatively, or in combination with the hardware circuitry described above, the logic (or logic unit or component) may be software in the form of one or more software modules, which may be configured to operate as its counterpart circuitry. The software modules may include, for example, an executable application, a daemon application, an application programming interface (API), a subroutine, a function, a procedure, a routine, source code, or even one or more instructions. The software module(s) may be stored in any type of a suitable non-transitory storage medium, such as a programmable circuit, a semiconductor memory, non-persistent storage such as volatile memory (e.g., any type of random access memory "RAM"), persistent storage such as non-volatile memory (e.g., read-only memory "ROM", power-backed RAM, flash memory, phase-change memory, etc.), a solid-state drive, hard disk drive, an optical disc drive, or a portable memory device.

The term "interconnect" may be construed as a physical or logical communication path between two or more components or devices including such components. For instance, a physical communication path may include a wired or wireless transmission medium. Examples of a wired transmission medium and a wireless transmission medium may include electrical wiring, optical fiber, cable, bus trace, a radio unit that supports radio frequency (RF) signaling, or any other conventional wired/wireless signaling transfer mechanism. A logical communication path may include any mechanism that allows for the exchange of content between different logic or components. Also, the terms "signaling" or "signal" generally refer to data in a prescribed format, such as an analog or a digital format for electrical signaling, light pulses for optical signaling, or the like. The data associated with the signaling may be propagated over an interconnect that supports the particular signaling type in accordance with a suitable transmission protocol.

For clarity, it is to be understood that the word "distal" refers to a direction relatively closer to a patient on which a medical device is to be used as described herein, while the word "proximal" refers to a direction relatively further from the patient. Also, the words "including," "has," and "having," as used herein, including the claims, shall have the same meaning as the word "comprising."

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Figure 1:
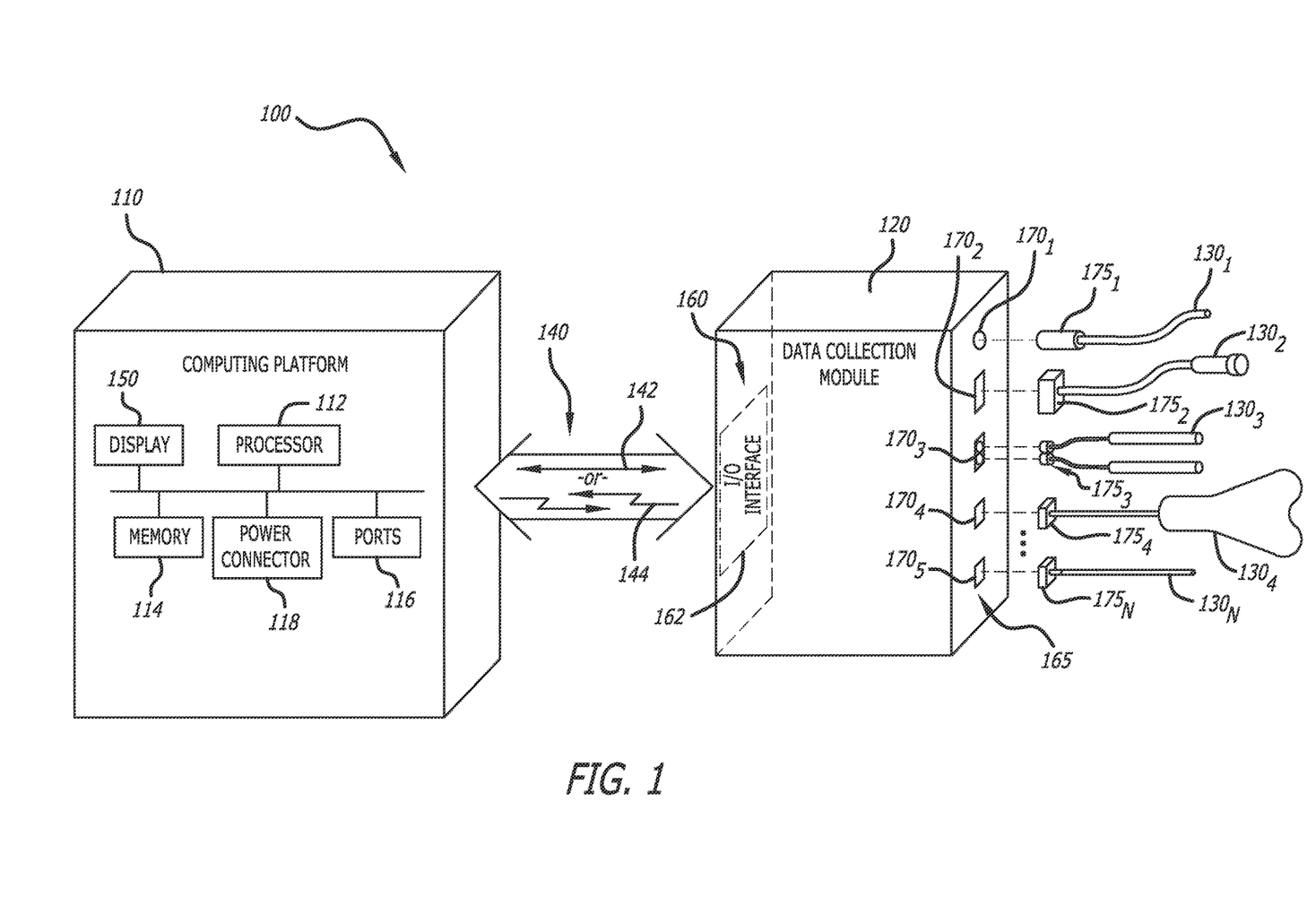
FIG. 1 is a first illustrative embodiment of a medical device monitoring system including an intermediary data collection module providing interconnectivity between the central computing platform and one or more medical devices.

Referring to FIG. 1, an illustrative embodiment of a medical device monitoring system 100 is shown. The medical device monitoring system 100 generally includes a computing platform 110 and a data collection module 120, which is communicatively coupled to the computing platform 110 and one or more medical devices $130_1$-$130_N$ ($N \geq 1$; $N=5$ for this embodiment). According to one embodiment of the disclosure, the data collection module 120 may be configured to operate as a vascular access data interpretation/transmission module, namely an interface configured to support the propagation of data associated with at least the placement and/or physical state (e.g., length, shape, form, and/or orientation) of a vascular access device from multiple (e.g., two or more) medical devices $130_1$-$130_5$ (e.g., N=5) to the computing platform 110. Each medical device $130_1$ . . . or $130_5$ features logic that provides data to the data collection module 120 to identify at least the placement and/or physical state (e.g., length, shape, form, and/or orientation) of a vascular access device within the vasculature of a patient. An example of a type of vascular access device may include, but is not limited or restricted to a catheter.

As shown, the data collection module 120 may be configured to be physically separate from the computing platform 110 (e.g., external module) and include logic that is capable of at least collecting subsets of data from different sources (e.g., medical devices $130_1$-$130_5$) without conducting analytics (e.g., computing/interpretation) on this collected data. The data collection module 120 supports communications with different types of medical devices that rely on different intravascular guidance technologies. For example, the medical devices $130_1$-$130_5$ may return data collected using optical technology (e.g., optical fiber), ultrasound technology (e.g., ultrasound probe), spatial technology (e.g., multiple electrodes with reliance of magnetic field effects) magnetic technology (e.g., multiple sensors), and/or an electrical technology (e.g., electrical interconnect).

In particular, according to one embodiment of the disclosure, the data collection module 120 may be configured to collect data from one or more medical devices $130_1$-$130_5$, where the type of collected data provides information as to the placement and/or physical state of a vascular access device being monitored by the medical device. For instance, when the medical device $130_1$ accompanies a vascular access device, the collected data may include, but is not limited or restricted to the following: (i) vascularization data associated with the structure and/or content of the vasculature of a patient into which the medical device $130_1$ is inserted, (ii) intravascular guidance data associated with the physical state (e.g., length, shape, form, and/or orientation) of the medical device $130_1$ for guidance and/or to determine its placement within the vasculature, and/or (iii) monitored data associated with a particular system or organ within the patient, or the like. When the medical device $130_1$ is positioned outside of the patient, the collected data may focus on the intravascular guidance, although vascularization and monitored data may be collected as described below.

Referring still to FIG. 1, the computing platform 110 is operably coupled to the data collection module 120 through an interconnect 140, such as a wired interconnect 142 or a wireless interconnect 144. Through this interconnect 140, the computing platform 110 is configured to receive data collected by the data collection module 120 from the medical device(s) $130_1$-$130_N$ upon which the computing platform 110 may perform analytics to produce analytic results, such as data to render a three-dimensional (3-D) representation of the vascular access device being monitored or perhaps a 3-D representation of the medical device when accompanying the vascular access device. The 3-D representation is provided to enable a clinician to monitor the location and/or physical state of the vascular access device. The analytic results may be displayed on a display 150 integrated into the computing platform 110 when the computing platform 110 is operating as a console. Alternatively, the computing platform 110 may be configured to conduct analytics on the collected data and transmit the analytic results to either (i) a display that is separate from the computing platform 110 or (ii) a networked device remotely located from the computing platform 110 that generates and/or provides results (e.g., rendering visually or audibly) for review by a clinician. An illustrative example of certain components that may be deployed within the computing platform 110 are described in U.S. Pat. No. 10,159,531, the entire contents of which are incorporated by reference herein.

As an illustrative example, the computing platform 110 may include a processor 112, a memory 114, ports 116, and a power connector 118. The processor 112, with access to the memory 114 (e.g., non-volatile memory), is configured to control functionality of the system 100, thus operating as a control processor. The ports 116 are provided for communicative couplings to the data collection module 110 as well as optional peripherals such as a printer, storage media, keyboard, or the like. The ports 116, in one embodiment, may include Universal Serial Bus (USB) ports, though another port type or a combination of port types can be used. The power connector 118 is included with the computing platform 110 to enable an operable connection to an external power supply, although an internal power source (e.g., backup battery) may also be employed, either with or exclusive of the external power supply. The power connector 118 may be further configured to regulate power use and distribution, where the I/O selection logic and power source described for the data collection module 120 as employed within the computing platform 110.

Referring still to FIG. 1, according to one embodiment of the disclosure, the data collection module 120 includes a first I/O interface 160 supporting communications with the computing platform 110 via the interconnect 140 and a second I/O interface 165 supporting communications with the medical devices $130_1$-$130_N$ via corresponding interconnects $175_1$-$175_N$. In particular, the first I/O interface 160 may be deployed as a physical or logical connector 162 to receive signaling over the wired interconnect 142. Alternatively, the first I/O interface 160 may be deployed as a wireless transceiver (e.g., wireless chip set including a wireless receiver and transmitter) to support communications with the computing platform 110 over the wireless interconnect 144. The second I/O interface 165 may be deployed as one or more connectors, each configured to support communications with a medical device $130_1$-$130_N$. For example, each of the one or more connectors may support a physical connection with another connector implemented at a proximal end of one of the medical devices $130_1$-$130_N$. As another example, each one or more connectors may be communicatively coupled to the medical devices $130_1$-$130_N$, where the communicative coupling may be a mating between separate physical connectors, a hardwired coupling between connectors associated with the data collection module 120 and one or more of the medical devices $130_1$-$130_N$, or any other type of type of connection (e.g., activator/magnetizer coupling) to enable communications between the data collection module 120 and one or more of the medical devices $130_1$-$130_N$.

More specifically, according to one embodiment of the disclosure, the second I/O interface 165 may include a plurality of I/O connectors $170_1$-$170_N$, where each I/O connector $170_1$-$170_N$ is configured to mate with connectors $175_1$-$175_N$ associated with a corresponding medical devices $130_1$-$130_N$, respectively. The mating may be removable or permanent (hardwired). It is noted that each of the mating connector pairs $170_1$ & $175_1$, $170_2$ & $175_2$, $170_3$ & $175_3$, $170_4$ & $175_4$, and $170_5$ & $175_5$ may correspond to (1) separate physical connectors that are connected together, (2) two different interfaces with a hardwired (or activator/magnetizer) connection between one or more internal components of the data collection module 120 and a corresponding medical device $130_1$, or the like.

For instance, as an illustrative example, the second I/O interface 165 may include an I/O connector $170_1$, which is configured to mate with an optical connector $175_1$ located at a proximal end of a multi-core optical fiber operating at least as part of the medical device $130_1$ (e.g., three-dimensional sensing stylet). Additionally, or in the alternative, the second I/O interface 165 may include (i) an I/O connector $170_2$ for mating with a connector $175_2$ associated with a second medical device $130_2$ such as an ultrasound probe (e.g., connector $175_2$ located on the second medical device $130_2$ or on an interconnect associated with the second medical device $130_2$); (ii) an I/O connector $170_3$ for mating with a connector $175_3$ associated with a third medical device $130_3$ such as multiple electrodes upon which a difference between emitted and received magnetic field measurements at different locations surrounding a body of the patient are used for imaging (e.g., connector $175_3$ located on the third medical device $130_3$ or on an interconnect associated with the third medical device $130_3$); (iii) an I/O connector $170_4$ for mating with a connector $175_4$ located on a fourth medical device $130_4$ or on an interconnect associated with the fourth medical device $130_4$ such as a magnetic sensor for tip location navigation; and/or (iv) an I/O connector $170_5$ for mating with a connector $175_5$ associated with a fifth medical device $130_5$ such as a sensor for at least receipt of signaling from a targeted source within a patient (e.g., electrical sensor deployed at a distal end of the medical device $130_5$ to provide electrocardiogram "ECG" signals).

Herein, the data collection module 120 (or each distinct data collection module 450/550 described below) may be used as a point of reference for plane identification/orientation, central line identification, malposition identification associated with the medical device, such as the stylet including the optical fiber $130_1$. Also, the data collection module (or each distinct module 450/550 described below) may exist as an in-the-bed module, deployed under a sterile drape with a thru barrier/window, and therefore, one or more intermediary I/O connectors may be needed to establish a communicative coupling between the computing platform 110 and the data collection module (or modules 450/550 of FIGS. 4A/5A).

Figure 2:
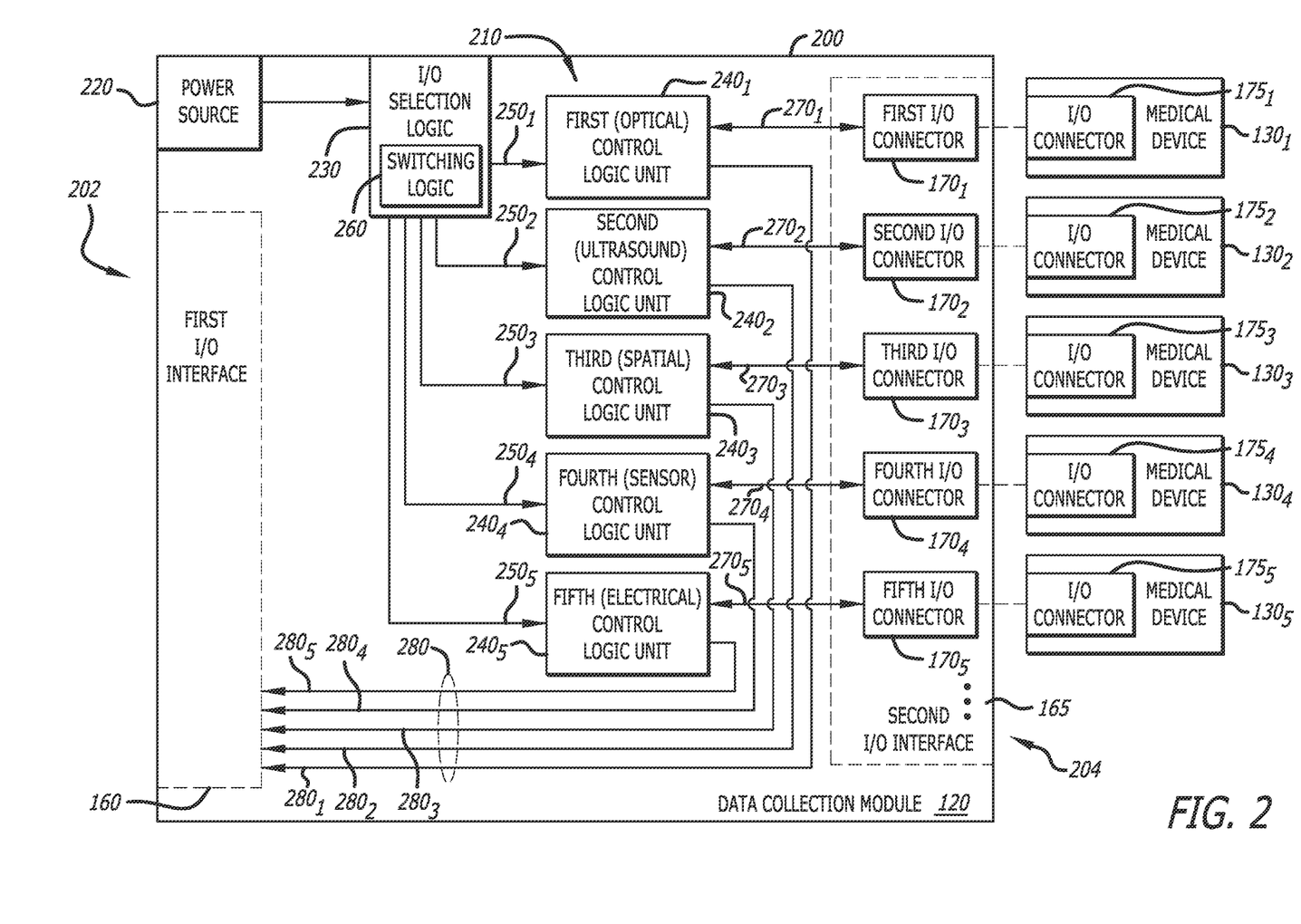
FIG. 2 is an exemplary embodiment of components deployed within the data collection module of FIG. 1 that provides connectivity between one or more medical devices and the centralized computing platform.

Referring now to FIG. 2, an exemplary embodiment of the data collection module 120 and the internal components deployed therein are shown. According to this embodiment, the data collection module 120 features a housing 200 made entirely or partially of a rigid material (e.g., hardened plastic, metal, glass, composite, or any combination thereof). The housing 200 provides access to the connector 162 associated with the first I/O interface 160 and the connectors $170_1$-$170_N$ associated with the second I/O interface 165 while, at the same time, protecting its internal components 210 from environmental conditions. As shown, the first I/O interface 160 may be positioned at a first area 202 of the housing 200 while the second I/O interface 165 may be positioned at the second area 204 of the housing 200. Herein, the first area 202 may be located on a side of the housing 200 opposite to the second area 204. Alternatively, one of the first or second areas 202 or 204 may be located on a front or back surface of the housing 200 while the other of the first or second areas 202 or 204 may be located on a lateral (or side) surface of the housing 200.

As shown in FIG. 2, as an illustrative example, the internal components 210 of the data collection module 120 features a power source 220 (e.g., power connector/regulator for an external power supply, internal power supply such as a battery back-up, etc.), I/O selection logic 230, and a plurality of control logic units $240_1$-$240_N$, which may correspond in number (N) to the number of I/O connectors $170_1$-$170_N$ or the number of medical devices $130_1$-$130_N$ supported by the data collection module 120. For this embodiment of the disclosure, the plurality of control logic units $240_1$-$240_N$ may include a first (optical) control logic unit $240_1$, a second (ultrasound) control logic unit $240_2$, a third (spatial) control logic unit $240_3$, a fourth (sensor) logic unit $240_4$, and a fifth (electrical) control logic unit $240_5$. Coupled to connectors $170_1$-$170_5$, the control logic units $240_1$-$240_5$ correspond to components that at least partially control operability of the medical devices $130_1$-$130_5$, respectively.

According to one embodiment of the disclosure, the I/O selection logic 230 is configured to select one or more of the medical devices $130_1$-$130_5$ to be powered and operational. The selection as to which medical device or medical devices $130_1$-$130_5$ is(are) powered and operational may be controlled automatically (without user intervention) based on connectivity of any of medical devices $130_1$-$130_5$ to their assigned connector $170_1$-$170_5$ of the data collection module 120. Stated differently, the connection of any medical device $130_1$, . . . , or $130_5$ to its corresponding connector $170_1$, . . . , or $170_5$ would be detected by the I/O selecting logic 230, and as a result, the I/O selection logic 230 would allow a supply of power from the power source 220 to one or more control logic units $240_1$, . . . , and/or $240_5$ via power interconnects $250_1$-$250_5$. For example, the I/O selection logic 230 may be configured to detect a connection of the first medical device $130_1$ (e.g., multi-core optical fiber stylet) being coupled to the first connector $170_1$, which would cause the I/O selection logic 230 to allow power to be supplied from the power source 220 to the first (optical) control logic unit $240_1$. Such detection may be accomplished through sense lines (not shown) that may be used to detect whether the first medical device $130_1$ is coupled to the first connector $170_1$.

Alternatively, the I/O selection logic 230 is configured to allow a clinician to manually select which of the medical devices $130_1$-$130_5$ currently connected to the data collection module 120, if any, is(are) to be powered and operational. According to one embodiment of the disclosure, the I/O selection logic 230 may include switching logic 260 (e.g., one or more switches, crossbar switch, etc.) actuated by one or more physical component (e.g., buttons, knobs, toggle switch, etc.) or a logical component selectable element on a display (e.g., LED (light emitting diode), LCD (liquid crystal display), etc.) accessible on the housing 200 (or positioned at the computing platform 110 with signaling directed to the I/O selection logic 230). For this embodiment of the disclosure, accessible via the housing 200, the switching logic 260 allows a clinician to select any combination of one or more of the medical devices $130_1$-$130_5$ to be in operation. Upon selection, the control logic unit $240_1$-$240_5$ corresponding to the selected medical device(s) $130_1$, . . . , and/or $130_5$ is powered by the power source 220. Based on a triggering event, such as activation of a physical actuator (e.g. depressible button, turning a knob, movement of a toggle switch) and/or activation of a virtual actuator (e.g., selectable element on a graphical user interface), a clinician may select one or more of the control logic units $240_1$-$240_5$ (and thereby one or more of the medical devices $130_1$-$130_5$) to be powered and capable of being used in the identification of the placement and/or physical state of the vascular access device (or a medical device accompanying the vascular access device).

Alternatively, in the event that the I/O selection logic 230 and the power source 220 are deployed within the computing platform 110 as described above, the data collection module 120 would still include any combination of the plurality of control logic units $240_1$-$240_5$, where power may be provided from the computing platform 110 via the first I/O interface 160.

As further shown, the plurality of control logic units $240_1$-$240_5$ include the first (optical) control logic unit $240_1$, the second (ultrasound) control logic unit $240_2$, the third (spatial) control logic unit $240_3$, the fourth (sensor) control logic unit $240_4$ and the fifth (electrical) control logic unit $240_5$. These control logic units $240_1$-$240_5$ may be configured to at least collect data from the medical devices $130_1$-$130_5$, where such data may be directed to placement of a vascular access device (e.g. catheter, etc.) within the vasculature of a patient. Some of these medical devices $130_1$, $130_4$ and/or $130_5$ may generate data applicable to the placement of the vascular access device when accompanying the vascular access device within the patient while other of these medical devices $130_2$ and/or $130_3$ may generate data applicable to the placement of the vascular access device when positioned proximate to and outside the patient. The collected data may be received over data interconnect 270 (e.g., interconnects $270_1$-$270_5$), where such data may be converted into digital signaling for transmission to the first I/O interface 160 over data interconnect 280 (e.g., interconnects $280_1$-$280_5$).

As an illustrative example, upon activation, the first (optical) control logic unit $240_1$ is powered so as to initiate incident light to the medical device $130_1$, which may be inserted into a luer connector of a catheter and reflects to incident light for receipt by the first control logic unit $240_1$ over data interconnect $270_1$. Within the first control logic unit $240_1$, the reflected light may be converted into an electrical signal for transmission to the computing platform 110 for analytics via data interconnect $280_1$ and the first I/O interface 160. As another illustrative example, the third (spatial) control logic unit $240_3$ is powered to provide electrical signaling to a plurality of electrodes $130_3$ be positioned on different sides of the patient to monitor movement and subsequent placement of a vascular access device within the vasculature of the patient based on measured magnetic field differences. The magnetic field differences are returned as electrical signaling to the third control logic unit $240_3$ via data interconnect $270_3$. Within the third control logic unit $240_3$, forwards these measured results to the computing platform 110 for analytics via data interconnect $280_3$ and the first I/O interface 160.

Figure 3A:
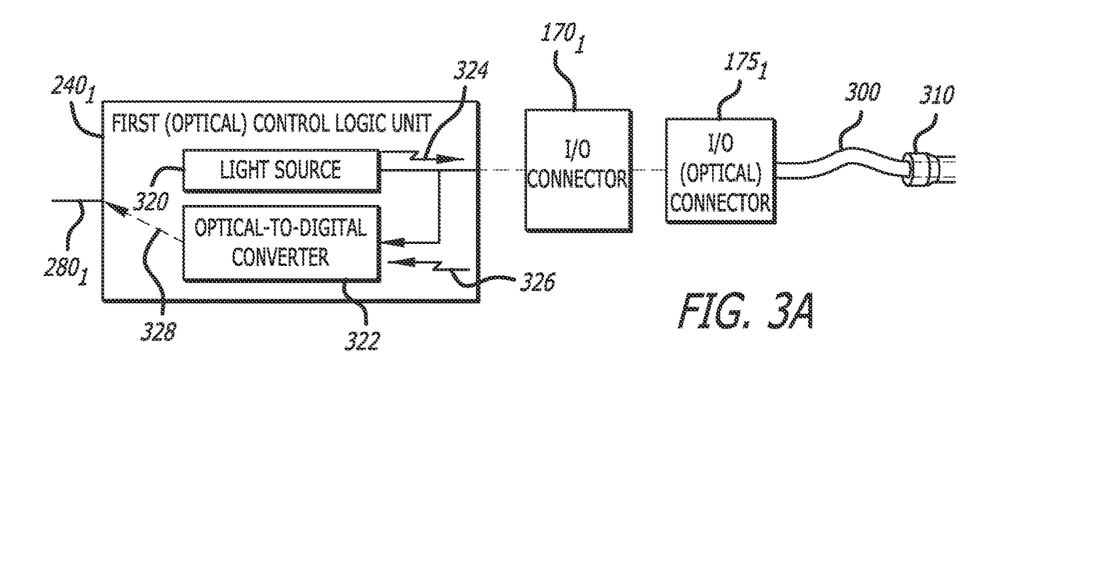
FIG. 3A is an exemplary embodiment of fiber control logic unit deployed within the data collection module of FIG. 2 to enable operational communications with a medical device including optical fiber-based functionality.

Referring to FIGS. 3A-3E, exemplary embodiments of the control logic units $240_1$-$240_5$ of FIG. 2 is shown. Herein, as shown in FIG. 3A, an illustrative embodiment of the first (optical) control logic unit $240_1$, which is configured to monitor physical state and placement of an optical fiber 300 (e.g., multi-core optical fiber), is shown. In particular, the optical fiber 300 may be part of the medical device (stylet) $130_1$, which is inserted into a portion of a vascular access device 310, such as an extension leg of a catheter for example. As a result, the physical state and placement of the vascular access device 310 may be extrapolated from the physical state and placement of the optical fiber 300. The electronics deployed within the first control logic unit $240_1$ are intended to relocate components associated with supporting operability of the optical fiber 300 from the computing platform 110 into the data collection module 120 of FIGS. 1-2. According to one embodiment of the disclosure, the first control logic unit $240_1$ may be configured to include at least a light source 320 and an optical-to-digital converter 322, although other components that support the transmission and reception of light signals for subsequent analytics by the computing platform 110 may be deployed within the first control logic unit $240_1$.

In particular, according to this embodiment of the disclosure, the first control logic unit $240_1$ may be configured to receive signaling from the computing platform 110, which triggers the light source 320 to emit a light signal 324 to the optical connector $170_1$ of the data collection module 120 for transmission over the optical fiber 300. The light signal 324 may operate as incident light, where characteristics of the incident light signal (e.g., phase, etc.) may be used as a reference in a correlation to characteristics of reflected light returned to the optical connector $170_1$ from sensors distributed along one or more core fibers maintained within the optical fiber 300 (e.g., intrinsic sensors inscribed into the core such as fiber Bragg grating "FBG" sensors). Receiving the reflected light 326 from the optical connector $170_1$, the optical-to-digital converter 322 is responsible for converting the reflected light signals into electrical signals 328 that can be analyzed by the computing platform 100, as changes to the characteristics of the reflected signal may identify the physical location and orientation of the optical fiber 300 for rendering on the display 150 associated with the computing platform 110.

Figure 3B:
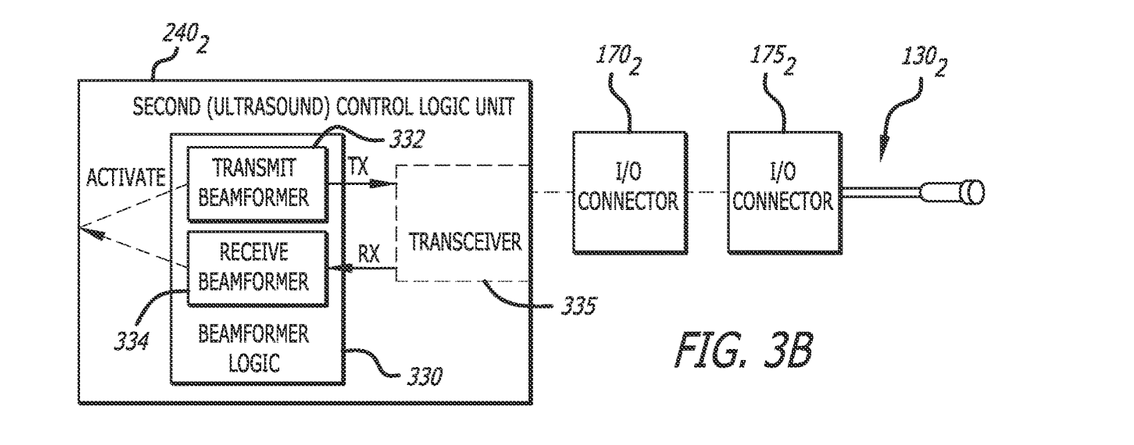
FIG. 3B is an exemplary embodiment of ultrasound control logic unit deployed within the data collection module of FIG. 2 to enable operational communications with an ultrasound probe.

Referring now to FIG. 3B, an illustrative embodiment of the second (ultrasound) control logic unit $240_2$ is shown. Herein, the second control logic unit $240_2$ includes beamformer logic 330 and a transceiver 335, which is communicatively coupled to the I/O connector $170_2$. Herein the beamformer logic 330 includes a transmit beamformer 332 and a receive beamformer 334. In particular, the transmit beamformer 332 is configured to emit signaling (e.g., electrical signals) in which the phase and/or relative amplitude of the signaling is controlled so that changes in phase and/or amplitude may be detected by the receive beamformer 334. The change in phase and/or amplitude may signify patterns of interference, where such interference can be used to discern shapes and/or positioning of a vascular access device within the vasculature of the patient.

In particular, the transmit beamformer 332, when activated, is configured to emit signaling with controlled phase and/or amplitude (e.g., prescribed electrical current). The signaling propagates from the transmit beamformer 332 to a medical device (e.g., ultrasound probe) $130_2$ via the transceiver 335 and the mated connectors $170_2$ and $175_2$. According to one embodiment of the disclosure, the transceiver 335 may perform certain signaling adjustments (e.g., filtering or other waveform shaping) prior to receipt by the ultrasound probe $130_2$. The transceiver 335 may further operate as a switch to control routing of signaling from the transmit beamformer 332 to the connector $170_2$ and from the connector $170_2$ to the receive beamformer 334. Alternatively, the transceiver 335 may be removed in which the connector $170_2$ features separate connector ports dedicated to transmit (TX) and receive (RX) communication paths for the ultrasound probe $130_2$.

Operating as a transducer, the ultrasound probe $130_2$ normally includes an array of quartz crystals, each configured to emit ultrasound waves into a patient's body when supplied with the signaling from the transmit beamformer 332. When the ultrasound probe $130_2$ is placed directly on a patient's body and moved over an area to be viewed, the ultrasound wave echoes (e.g., ultrasonic waves bouncing off items within the patient's body such as tissue masses, vascular access devices, etc.) are detected by the quartz crystals within the ultrasound probe $130_2$. The crystals produce electrical signals in response to the ultrasound wave echoes, which are returned to the beamformer receiver 334 via the I/O connector $170_2$ (and optionally the transceiver 335). Variations in the returned electrical signaling generate contrast on a sonogram rendered by the computing platform 110. The sonogram may be used to provide a visible representation of the placement and/or physical state of a vascular access device inside the patient.

Figure 3C:
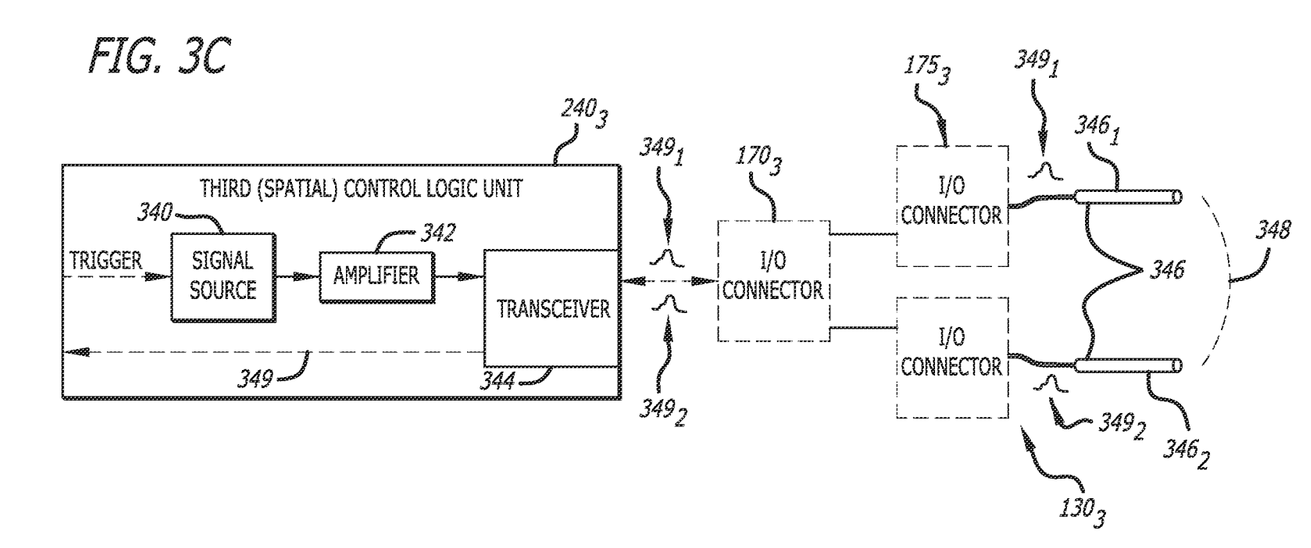
FIG. 3C is an exemplary embodiment of spatial control logic unit deployed within the data collection module of FIG. 2 to enable operational communications with a medical device including spatial evaluation functionality.

Referring to FIG. 3C, an illustrative embodiment of the third (spatial) control logic units $240_3$ that controls generation of one or more magnetic fields to detect the placement and/or physical state of a vascular access device is shown. Herein, the third control logic unit $240_3$ includes a signal source 340, an amplifier 342, and a transceiver 344. Upon a triggered event from the computing platform 110, the signal source 340 of the spatial control logic unit $240_3$ generates signaling, which is amplified by the amplifier 342 and may undergo waveform shaping by the transceiver 344 prior to transmission via the third I/O connector $170_3$. The amplified signaling is provided to the medical device $130_3$, namely as a reference signal to a first electrode $346_1$ of a plurality of electrodes 346.

In particular, according to one embodiment of the disclosure, the first electrode $346_1$ is configured to emit signaling $349_1$ that generates a magnetic field 348 detected by a second electrode $346_2$ of a plurality of electrodes 346. The second electrode $346_2$ may be positioned at a different location of the patient body in order to create the magnetic field 348 between the electrodes 346 to capture an image of the items within the patient's body (e.g., tissue masses, vascular access devices, etc.) between the electrodes 346. The second electrode $346_2$ receives signaling $349_2$ (e.g., electrical signals) associated with the magnetic field 348 and provides the detected signaling to the transceiver 344 via the third I/O connector $170_3$. The detected signaling $349_2$ may be returned to the computing platform 110. Giving that the reference signal may be fairly static in nature and the data associated with the reference signal is pre-stored, the computing platform 110 is configured to determine a measured difference between the reference signal and the detected signaling $349_2$, the computing platform may be able to generate imaging information that can be sent and provided to a clinician for review.

Figure 3D:
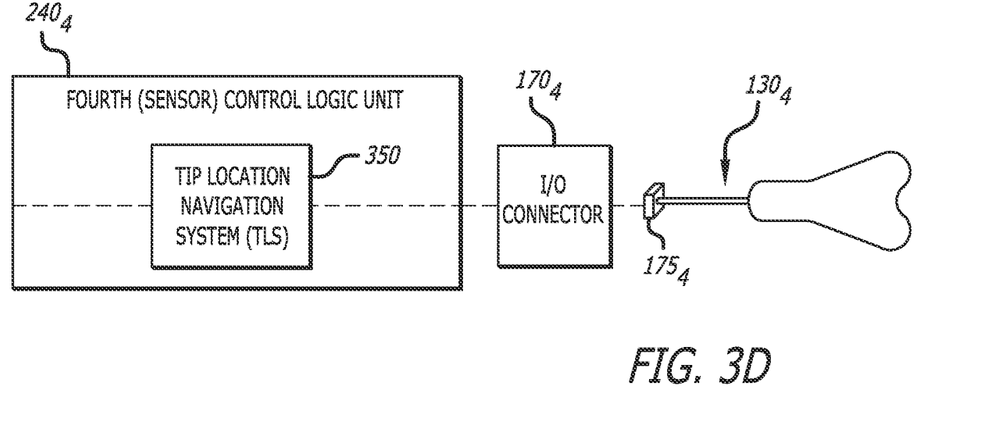
FIG. 3D is an exemplary embodiment of sensor control logic unit deployed within the data collection module of FIG. 2 to enable operational communications with a medical device including magnet sensors.

Referring now to FIG. 3D, an illustrative embodiment of the fourth (sensor) logic unit $240_4$ is shown. The fourth control logic unit $240_4$ includes a Tip Location Navigation System (TLS) 350, which is operationally coupled to the fourth I/O connector $170_4$. Herein, the fourth control logic unit $240_4$ is responsible for generating signaling for tip location of the medical device $130_4$ being inserted through the vascular structure of a patient in order to appropriately place the medical device to monitor the health of a patient. For instance, according to one embodiment, the TLS 350 of the fourth control logic unit $240_4$ may be used to control placement of an appropriate catheter near the heart of a patient in order to return ECG signaling to the computing platform 110 via the fifth control logic unit $240_5$. Therefore, the fourth control logic unit $240_4$ may operate in combination with other control logic units, such as the fifth control logic unit $240_5$ to control placement of an electrical wire to recover electrical signaling that pertains to operability of the heart. Alternatively, the TLS functionality may be deployed within any of the control logic unit $240_{1-3, 5}$ to provide additional TLS functionality.

Figure 3E:
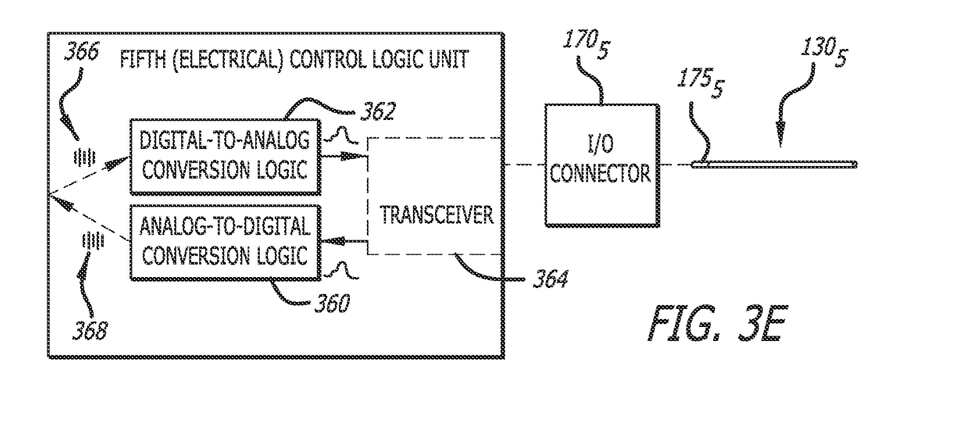
FIG. 3E is an exemplary embodiment of electrical control logic unit deployed within the data collection module of FIG. 2 to enable operational communications with a medical device including electrical signal-based functionality.

Referring now to FIG. 3E, an illustrative embodiment of the fifth (electrical) logic unit $240_5$ is shown. The fifth control logic unit $240_5$ is configured to at least receiving electrical signals (e.g., ECG signals, etc.) from the medical device $130_5$ for subsequent analytics by the computing platform 110. Additionally, the fifth control logic unit $240_5$ may be configured to transmit electrical signaling to the medical device $130_5$ to initiate the propagation of the received electrical signals described above. With respect to one embodiment of the disclosure, the fifth control logic unit $240_5$ includes analog-to-digital conversion logic 360 communicatively coupled to the fifth I/O connector $170_5$. According to another embodiment of the disclosure, the fifth control logic unit $240_5$ includes the analog-to-digital conversion logic 360, digital-to-analog conversion logic 362 and a transceiver 364, which is communicatively coupled to the fifth I/O connector $170_5$.

Herein, the fifth control logic unit $240_5$ may be configured to receive an electrical signal 368 for use as a reference signal, which is converted from a digital format to an analog format by the digital-to-analog conversion logic 362 prior to transmission over the fifth I/O connector $170_5$ to the medical device $130_5$. The transceiver 364 may be configured to operate as a switch to control transmission of the reference signaling and receive signaling from the medical device $130_5$ for routing to the analog-to-digital conversion logic 360. The analog-to-digital conversion logic 360 converts the received analog signal into a digital result 368 for transmission to the computing platform 110 to conduct analytics of the digital result 368 associated with the returned digital signal for rendering the results of these analytics (e.g., determined pulse representing rate, rhythm and strength of a monitored heart based on amplitude and periodicity of the analog signal, etc.).

Figure 4A:
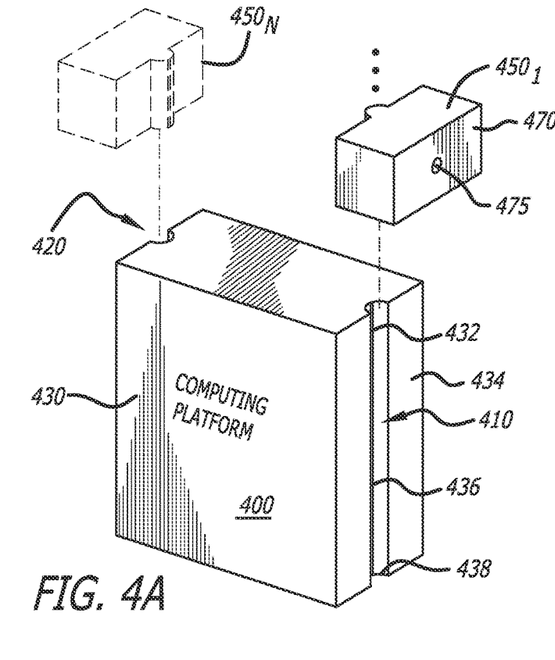
FIG. 4A is second illustrative embodiment of the medical device monitoring system including a central computing platform and one or more data collection modules that support connectivity with one or more medical devices.

FIG. 4A is a second illustrated embodiment of the medical device monitoring system 100 including a computing platform 400 and one or more data collection modules $450_1$-$450_N$ that support connectivity with one or more medical devices $130_1$-$130_N$ is shown. While the computing platform 400 may include internal components similar to those components of the computing platform 110 of FIG. 1 described above, the I/O relied upon for establishing communicative couplings to the data collection modules $450_1$-$450_N$ differ. For instance, one or more of the medical devices $130_1$-$130_N$ may be hardwired to its corresponding data collection modules $450_1$-$450_N$ (e.g., connector 475 and connector $175_1$ of FIGS. 4E-4F may represent logical interfaces between these two separate components) or one or more of the medical devices $130_1$-$130_N$ may be removably coupled to the data collection modules $450_1$-$450_N$ (e.g., connector 475 and connector $175_1$ of FIGS. 4E-4F may represent physical connectors that are used in coupling these two separate components). Also, in lieu of a single data collection module 120 of FIG. 1, each of the data collection modules $450_1$-$450_N$ is configured to support a specific type of intravascular guidance technology utilized by its respective medical device $130_1$-$130_N$ (e.g., fiber optic, ultrasound, spatial, magnetic sensing, or electrical), and thus, each of the data collection modules $450_1$-$450_N$ may be configured to include the components associated with the control logic units $240_1$-$240_N$, respectively (see FIGS. 3A-3E).

Herein, the data collection modules $450_1$-$450_N$ may be communicatively coupled to at least a first I/O interface 410, or alternatively a second I/O interface 420 when the computing platform 400 features a dual I/O interface architecture as shown. The communicative coupling may correspond to an electrical and mechanical (electro-mechanical) coupling, an optical and mechanical (opto-mechanical) coupling, or any other type of connection that allow for the transmission and/or reception of data between the computing platform 400 and a particular data collection module 450*i* (where 1≤i≤N). Herein, an electro-mechanical coupling between interconnects of both the interface 410 or 420 and the data collection module $450_i$ is achieved by sliding a data collection module $450_i$ along the first I/O interface 410 until the data collection module $450_i$ is set into a secured position. Snap locks or tabs set at certain locations along the interfaces 410/420 may be used.

Figure 4B:
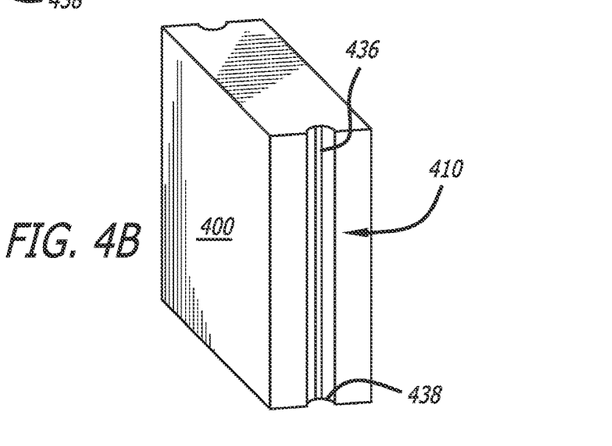
FIG. 4B is a perspective view of a first surface of the computing platform including an exemplary embodiment of a first input/output (I/O) interface of the computing platform.

Herein, as shown in FIGS. 4A & 4B, the computing platform 400 features a housing 430 that is formed to allow the data collection modules $450_1$-$450_N$ to be communicatively coupled to at least the first I/O interface 410. According to one embodiment of the disclosure, the housing 430 is made entirely or partially of a rigid material such as a hardened plastic or any insulative composite material. Also, the first I/O interface 410, which features a first channel 432 formed along a first surface 434 of the housing 430 with a first interconnect 436 positioned along an interior, concave surface 438 of the first channel 432. Alternatively, in lieu of this channel connectivity, the computing platform 400 may be configured with distinct ports at predetermined locations for communicative coupling with a distinct data collection module $450_1$ . . . , or $450_N$.

As shown, the first surface 434 may constitute a sidewall of the housing 430, where the first channel 432 is formed longitudinally (e.g., in a general vertical direction) along the sidewall 434. The length of the first channel 432 may extend longitudinally along a portion (e.g., ranging from 25-50%, 25%-75%, 50%-95%, etc.) of the sidewall 434 or along an entirety of the sidewall 434 as shown. Positioned along the interior, concave surface 438 of the first channel 432, the first interconnect 436 enables transmission and/or reception of signaling with any of the data collection modules $450_1$-$450_N$ communicatively coupled to the first I/O interface 410, in particular the first interconnect 436. Stated differently, the first interconnect 436 operates in a similar manner as the interconnect 142 of FIG. 1, as both interconnects being interposed between components of the computing platform and a counterpart data collection module(s).

Figure 4C:
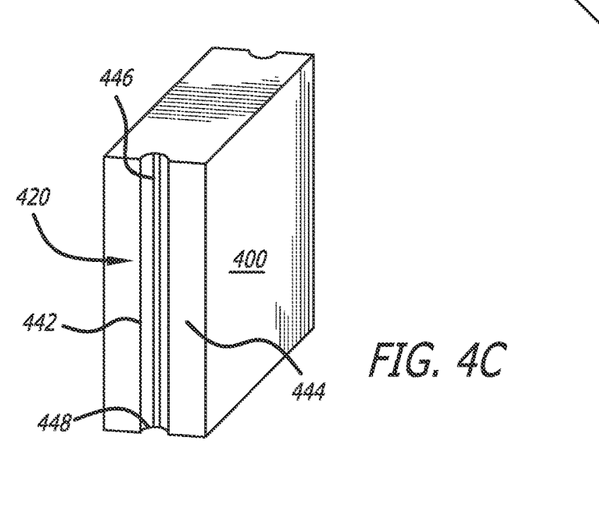
FIG. 4C is a perspective view of a second surface of the computing platform including an exemplary embodiment of a second I/O interface of the computing platform.

Additionally, as an optional feature as shown in FIGS. 4A & 4C, the computing platform 400 may include the second I/O interface 420, which features an architecture identical or at least substantially similar to the architecture of the first I/O interface 410. Herein, the second I/O interface 420 may be configured with a second channel 442 formed along a second surface 444 of the housing 430 with a second interconnect 446 positioned along an interior, concave surface 448 of the second channel 442. As shown, the second surface 444 may constitute a second sidewall of the housing 430, which is positioned on an opposite side of the housing 430. Alternatively, although not shown, the second surface 444 may constitute a surface orthogonal to the first surface 434 (e.g., a sidewall where the first surface 434 is a front or back surface of the housing; a front or back surface where the first surface 434 is a sidewall of the housing 430).

Referring to FIG. 4C, the second channel 442 is formed longitudinally (e.g., in a general vertical direction) along the sidewall 444. The length of the second channel 442 may extend longitudinally along a portion (e.g., ranging from 25-50%, 25%-75%, 50%-95%, etc.) of the sidewall 444 or along an entirety of the sidewall 444 as shown. Positioned along the interior, concave surface 448 of the second channel 442, the second interconnect 446 enables transmission and/or reception of signaling with any of the data collection modules $450_1$-$450_N$ communicatively coupled to the second interconnect 446 of the second I/O interface 420.

Figure 4D:
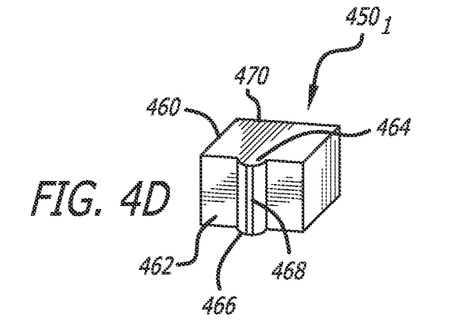
FIG. 4D is a perspective view of a data collection module that may be communicatively coupled to the computing platform of FIG. 4A.

Referring to FIGS. 4A & 4D, each of the data collection modules $450_1$-$450_N$ (e.g., data collection module $450_i$) is configured with a housing 460. The housing 460 features a first surface 462 including a protruding member 464 having an exterior, convex surface 466. The convex surface 466 is complementary with the concave surface 438 of the first channel 432 and the concave surface 448 of the second channel 442 of the computing platform 400. As shown, the surface 462 constitutes a front surface of the data collection module $450_1$ in which a back surface 470 of the housing 460 includes an I/O connector 475 that support a communicative coupling with a respective medical device $130_i$. As an illustrative example, for a first data collection module $450_1$, the I/O connector 475 may correspond any I/O connector $170_i$ ($1 \leq i \leq N$), such as I/O connector $170_1$ configured to establish a communicative coupling (e.g., optical-mechanical coupling) with the I/O connector $175_1$ of the medical device $130_1$.

Positioned along at least a portion of the convex surface 466 of the protruding member 464, a third interconnect 468 is oriented to establish a communicative coupling with either the first interconnect 436 of the first I/O interface 410 or the second interconnect 446 of the second I/O interface 420. As a result, when communicatively coupled to the first I/O interface 410, the data collection module $450_i$ is oriented so that the I/O connector 475 is accessible, which allow a clinician to communicatively couple an I/O connector of a medical device to the I/O connector 475. This connection enables the clinician to utilize the medical device $130_i$ for vascular access device monitoring, as described above.

Figure 4E:
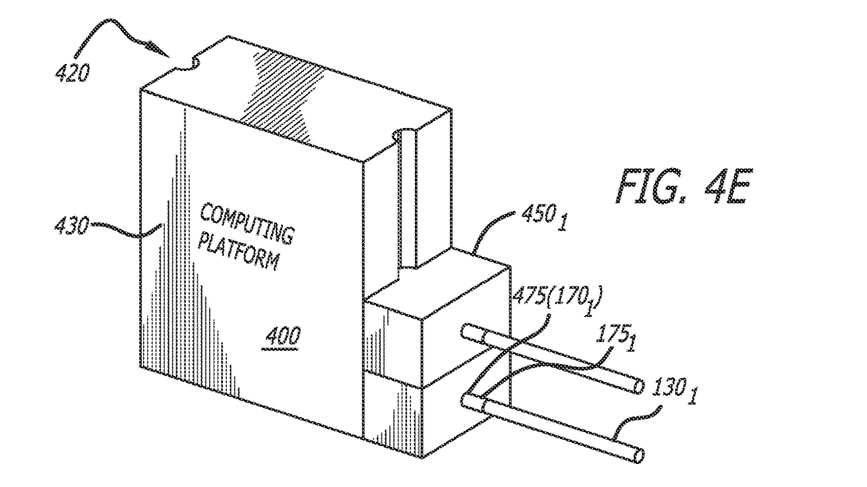
FIG. 4E is an exemplary embodiment of the medical device monitoring system including data collection modules stacked and communicatively coupled to the second I/O interface of the computing platform.
Figure 4F:
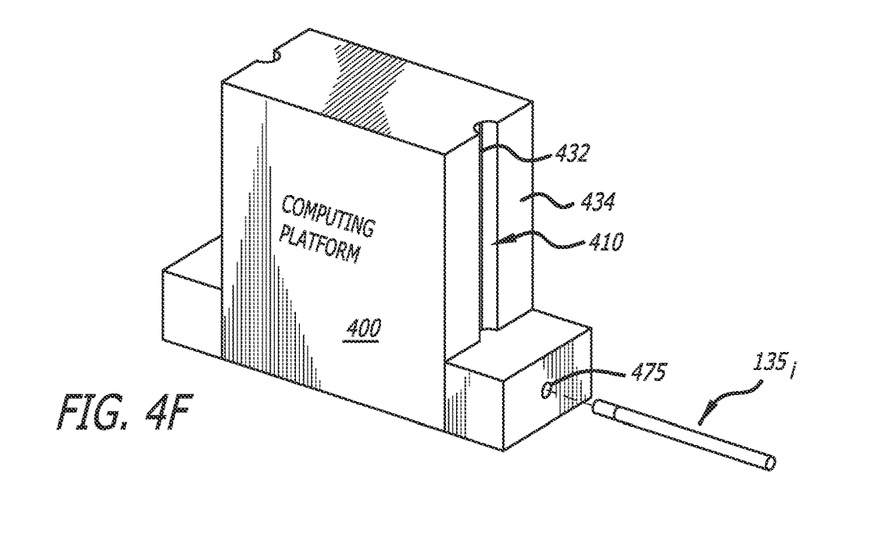
FIG. 4F is an exemplary embodiment of the medical device monitoring system including data collection modules communicatively coupled to each of the first I/O interface and the second I/O interface of the computing platform.
Figure 5A:
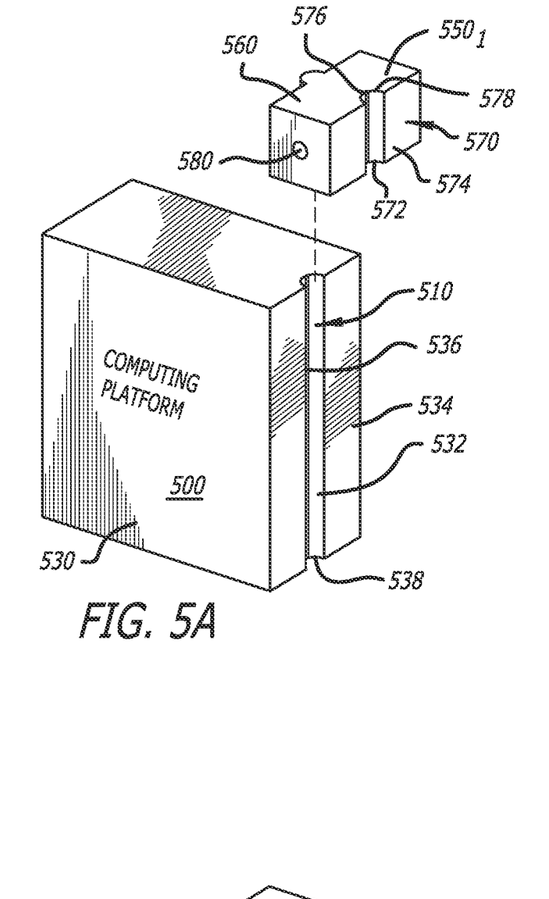
FIG. 5A is a third illustrated embodiment of the medical device monitoring system.

As shown in FIG. 4E, one or more data collection modules $450_1$-$450_N$ (e.g., data collection module $450_1$) may be communicatively coupled to the first I/O interface 410 while at least another data collection module (e.g., data collection module $450_2$) may be communicatively coupled to the second I/O interface 420. As shown, different types of data collection modules (e.g., optical and ultrasound, optical and spatial, electrical and ultrasound, etc.) may be positioned at different I/O interfaces, although the computing platform 400 may be configured to support the same types of data collection modules (e.g., two optical data collection modules $450_1$) communicatively coupled to different I/O interfaces 410 and 420. Additionally, or in the alternative, as shown in FIG. 4F, two or more of the data collection modules $450_1$-$450_N$ may be communicatively coupled to a single I/O interface (e.g., the first I/O interface 410) and arranged in a stacked configuration. As before, the data collection modules $450_1$-$450_N$ may be directed to different types of intravascular guidance technologies or the same specific type of intravascular guidance technology.

As an alternative embodiment, although not illustrated, the first I/O interface 410 and/or the second I/O interface 420 of the computing platform 400 may be deployed with a protruding (convex) interface (similar in architecture to the interface members 462-468 for the data collection module $450_1$) while the data collection module $450_1$ may include a concave interface (similar in architecture to interface members 432-438 of the first I/O interface 410 and/or interface members 442-448 of the second I/O interface 420). Other types of interfaces (e.g., any male/female type of adapters, etc.) may be used. The selected I/O interface configurations described above and illustrated in FIGS. 4A-4F as well as FIGS. 5A-FD are provided for illustrative purpose.

FIG. 5A is a third illustrated embodiment of the medical device monitoring system 100 including a computing platform 500 and one or more data collection modules $550_1$-$550_N$ that support connectivity with one or more medical devices $130_1$-$130_N$ is shown. The data collection modules $550_1$-$550_N$ may be operationally equivalent to the data collection modules $450_1$-$450_N$ of FIGS. 4A-4F, but its housing construction and I/O connector layout differ. Herein, the data collection modules $550_1$-$550_N$ may be communicatively coupled to at least a first I/O interface 510, or alternatively a second I/O interface (not shown) when the computing platform 500 features a dual I/O interface architecture.

Figure 5B:
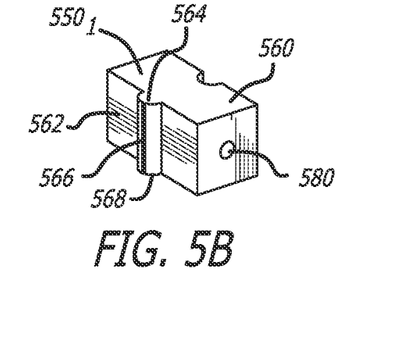
FIG. 5B is a perspective view directed to a first surface of an exemplary embodiment of the data collection module for communicative coupling with the computing platform of FIG. 5A.
Figure 5C:
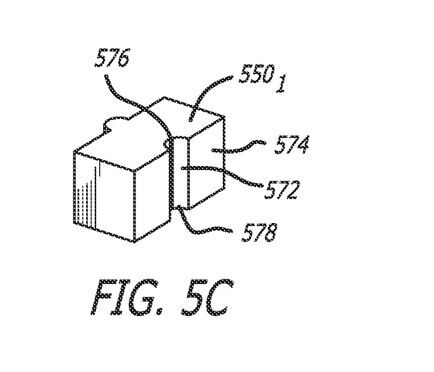
FIG. 5C is a perspective view directed to a second surface of an exemplary embodiment of the data collection module for communicative coupling with another data collection module.
Figure 5D:
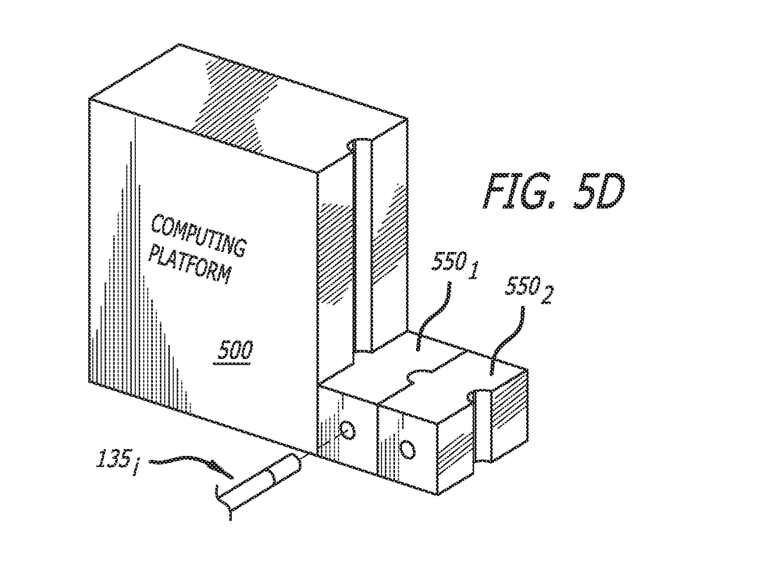
FIG. 5D is an exemplary embodiment of the medical device monitoring system including multiple data collection modules with serial connectivity to the computing platform.

Herein, as shown in FIGS. 5A & 5D, the computing platform 500 features a housing 530 that is formed to allow the data collection modules $550_1$-$550_N$ to be communicatively coupled to the first I/O interface 510. As described above, the housing 530 may be made entirely or partially of a rigid material such as a hardened plastic or any insulative composite material. Also, the first I/O interface 510, which features a first channel 532 formed along a first surface 534 of the housing 530 with a first interconnect 536 positioned along an interior, concave surface 538 of the first channel 532. As previously described, in lieu of this channel connectivity, the computing platform 500 may be configured with distinct ports at predetermined locations for communicative coupling with a distinct data collection module $550_1 \ldots$, or $550_N$.

As shown, the first surface 534 may constitute a sidewall of the housing 530, where the first channel 532 is formed longitudinally along a portion of the length of the sidewall 534 or its entirety. Positioned along the concave surface 538 of the first channel 532, the first interconnect 536 enables transmission and/or reception of signaling with one or more of the data collection modules $550_1$-$550_N$, depending on the stacking orientation. Stated differently, the first interconnect 536 is configured to establish a direct communication coupling with one or more of the stackable, data collection modules $550_1$-$550_N$ (e.g., data collection module $550_1$), but each the data collection modules further includes an interconnect that operates as an intermediary communicative coupling to the first interconnect 536.

More specifically, as shown in FIGS. 5A-5C, each of the data collection modules $550_1$-$550_N$ (e.g., data collection module $550_i$) is configured with a housing 560. The housing 560 features a first surface 562 including a protruding member 564 with a second interconnect 566 positioned on an exterior, convex surface 568 for establishing a communicative coupling with the first interconnect 536 of the computing platform 500. Additionally, each of the data collection modules $550_1$-$550_N$ (e.g., data collection module $550_i$) further features a second surface 570, which includes a channel 572 formed along the second surface 574 of the housing 560 with a third interconnect 576 positioned along an interior, concave surface 578 of the channel 572. Herein, the convex surface 568 of the protruding member 564 is complementary with both concave surface 538 of the first channel 532 of the computing platform 500 and the concave surface 578 of the channel 572 of any of the other data collection modules.

According to one embodiment of the disclosure, the second surface 570 may constitute a surface that is on an opposite side of the housing 530 as the first surface 562 or on a side generally orthogonal to the first surface 562. Therefore, when the first surface 562 constitutes a front side of the data collection module $550_i$, the second surface 570 may constitute a front side, back side, or opposite sidewall of the housing 560. Similarly, where the first side surface 562 constitutes a sidewall of the housing 560, the second surface 570 may constitute the either an opposite sidewall, front side or back side of the housing 530. As a result, the data collection module 550$_i$ is oriented so that an I/O connector 580 (e.g., any I/O connector 170$_i$ of FIG. 1 or I/O connector 475 of FIG. 4A) may be accessible on a surface of the housing 530 other than the first or second surfaces 562 and 570, which allow a clinician to communicatively couple the medical device 130$_i$ to the I/O connector 580. For instance, a medical device (e.g., medical device 130$_i$) may be hardwired to its corresponding data collection module 550$_1$ or the medical devices 130$_i$ may be removably coupled to the data collection module 550$_1$ (see FIG. 5D). This connection enables the clinician to utilize the medical device 130$_i$ for vascular access device monitoring, as described above.

More specifically, as shown in FIG. 5D, positioned along at least a portion of the convex surface 568 of the protruding member 564 of the data collection module 550$_i$ (e.g., data collection module 550$_1$), the second interconnect 566 is oriented to establish a direct communicative coupling with the first interconnect 536 of the first I/O interface 510 of the computing platform 500. Additionally, the third interconnect 576 provides an indirect communicative coupling (e.g., electrical connection) between the first interconnect 536 of the computing platform 500 and a second interconnect of another data collection module 550$_{i+1}$ (e.g., data collection module 550$_2$). This enables the data collection modules 550$_1$-550$_N$ to be stacked and also connected in a serial (lateral) manner.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A medical device monitoring system, comprising:
   a computing platform including a first housing that houses a processor and a memory; and
   a data collection module including:
      a second housing distinct from the first housing,
      a first input/output (I/O) interface configured to establish a first communicative coupling with the computing platform,
      a second I/O interface including one or more connectors; and
      one or more control logic units deployed to operate within the second housing, wherein each control logic unit of the one or more control logic units is configured to (a) communicatively couple to a separate connector of the one or more connectors of the second I/O interface, (b) control operations of a medical device being communicatively coupled to the separate connector, and (c) collect a subset of data acquired at least during placement of a vascular access device within a vasculature of a patient.

2. The medical device monitoring system as defined in claim 1, wherein the medical device is communicatively coupled to the second I/O interface when the medical device is hardwired to the second I/O interface.

3. The medical device monitoring system as defined in claim 1, wherein the subset of data collected by the data collection module comprises vascularization data associated with a structure or content of the vasculature of the patient.

4. The medical device monitoring system as defined in claim 1, wherein the subset of data collected by the data collection module comprises intravascular guidance data associated with a physical state of the vascular access device for guidance and determination of placement of the vascular access device within the vasculature of the patient.

5. The medical device monitoring system as defined in claim 1, wherein the subset of data collected by the data collection module comprises intravascular guidance data associated with a physical state of the medical device when accompanying the vascular access device being inserted within the vasculature of the patient, the physical state of the medical device including a shape, a form, or an orientation of the medical device.

6. The medical device monitoring system as defined in claim 1, wherein the second I/O interface of the data collection module is communicatively coupled to the medical device corresponding to a three-dimensional sensing stylet, the three dimensional sensing stylet includes a multi-core optical fiber with a proximal end of the multi-core optical fiber being communicatively coupled with the second I/O interface.

7. The medical device monitoring system as defined in claim 6, wherein the medical device is communicatively coupled by hardwiring an interconnect being part of the medical device with the second I/O interface.

8. The medical device monitoring system as defined in claim 1, wherein the one or more control logic units of the data collection module comprises (i) a first control logic unit to emit incident light through core fibers of a multi-core optical fiber of a three-dimensional sensing stylet corresponding to a first medical device and receive reflected light as the subset of data and (ii) a second control logic unit to provide signaling to an ultrasound probe and receive signaling corresponding to the subset of data acquired from the ultrasound probe to provide guidance for placement of the vascular access device within the patient.

9. The medical device monitoring system as defined in claim 1, the computing platform to conduct analytics on at least a portion of the subset of data from any of the one or more control logic units to determine a physical state of the vascular access device or the medical device.

10. The medical device monitoring system as defined in claim 9, wherein the computing platform comprises an integrated display for rendering of the analytics.

11. The medical device monitoring system as defined in claim 9, wherein the subset of data acquired by the computing platform is to produce analytic results, the analytic results including data to render a three-dimensional (3-D) representation of the vascular access device being monitored or a 3-D representation of the medical device when accompanying the vascular access device.

12. The medical device monitoring system as defined in claim 1, wherein the vascular access device is a catheter.

13. A medical device monitoring system 1, comprising:
    a computing platform including:
       a first input/output (I/O) interface including a first interconnect, and
       a first housing that houses a processor configured to receive data routed over the first interconnect, the processor to conduct analytics on the received data; and one or more data collection modules configured to be communicatively coupled to a computing device, wherein each of the one or more data collection modules includes a housing, a computing platform I/O interface, a medical device I/O interface including a connector, and a control logic unit that is configured to:
communicatively couple to the connector,
control operations of a distinct medical device, and
collect a subset of data acquired by the distinct medical device at least during placement of a vascular access device within a vasculature of a patient, wherein the computing platform I/O interface is configured to establish a communicative coupling with the first I/O interface of the computing platform.

14. The medical device monitoring system as defined in claim 13, wherein each data collection module of the one or more data collection modules includes at least (i) a second interconnect configured to be communicatively couple with the first interconnect when each data collection module is coupled to the computing platform to provide collected data to the computing platform upon which analytics are performed to determine a placement or physical state of the vascular access device.

15. The medical device monitoring system as defined in claim 13, wherein the first I/O interface comprises a channel in which the first interconnect resides.

16. The medical device monitoring system as defined in claim 15, wherein each data collection module of the one or more data collection modules comprises a protrusion, the protrusion being sized to reside with the channel and including a second interconnect that establishes the communicative coupling with the first interconnect when the protrusion resides within the channel.

17. The medical device monitoring system as defined in claim 16, wherein the first I/O interface is of a concave arrangement and the protrusion for each data collection module of the one or more data collection modules is of a convex arrangement with a same radius of curvature as the concave arrangement.

18. The medical device monitoring system as defined in claim 13, wherein each of the one or more data collection modules is stacked vertically with a corresponding connector for mating with a connector of the distinct medical device on a side uncovered by a neighboring data collection module.

19. The medical device monitoring system as defined in claim 13, wherein the first I/O interface of the computing platform comprises a first channel in which the first interconnect resides.

20. The medical device monitoring system as defined in claim 19, wherein each data collection module of the one or more data collection modules comprises a protrusion extending from a first surface of a housing of each data collection module and a second channel formed along a second surface of the housing of each data collection module, the protrusion being sized to reside with the first channel and including a second interconnect that establishes a communicative coupling with the first interconnect when the protrusion resides within the first channel.

21. The medical device monitoring system as defined in claim 20, wherein the second channel of at least a first data collection module of the one or more data collection modules includes a third interconnect and is sized to receive a protrusion of a second data collection module of the one or more data collection modules, the protrusion of the second data collection module including the second interconnect.

22. The medical device monitoring system as defined in claim 21, wherein each of the one or more data collection modules is arranged laterally with a corresponding connector for mating with a connector of a distinct medical device being positioned on a surface other than the first surface and the second surface.

23. The medical device monitoring system as defined in claim 19, wherein each data collection module of the one or more data collection modules comprises the first channel in which a second interconnect resides, the second interconnect configured to be communicatively couple with the first interconnect associated with the first I/O interface when each data collection module is communicatively coupled to the computing platform.

24. The medical device monitoring system as defined in claim 23, wherein the first I/O interface of the computing platform comprises a protrusion extending from a first surface of a housing of the computing platform, the protrusion being sized to reside with the first channel of the first data collection module and the first interconnect positioned on the protrusion to physically contact the second interconnect of the second data collection module.

25. The medical device monitoring system as defined in claim 1, wherein a first control logic unit of the one or more control logic units is configured to communicatively couple to a first connector of the one or more connectors and control operations of a first medical device communicatively coupled to the first connector, and wherein a second control logic unit of the one or more control logic units is configured to communicatively couple to a second connector of the one or more connectors and control operations of a second medical device communicatively coupled to the second connector.

* * * * *